US009512200B2

(12) United States Patent
Deisher

(10) Patent No.: US 9,512,200 B2
(45) Date of Patent: Dec. 6, 2016

(54) PERSONALIZED PRODUCTION OF BIOLOGICS AND METHOD FOR REPROGRAMMING SOMATIC CELLS

(75) Inventor: Theresa A. Deisher, Seattle, WA (US)

(73) Assignee: AVM Biotechnology, LLC, Seattle, WA (US)

( * ) Notice: Subject to any disclaimer, the term of this patent is extended or adjusted under 35 U.S.C. 154(b) by 492 days.

(21) Appl. No.: 13/342,704

(22) Filed: Jan. 3, 2012

(65) Prior Publication Data

US 2012/0171722 A1   Jul. 5, 2012

Related U.S. Application Data

(60) Provisional application No. 61/429,409, filed on Jan. 3, 2011, provisional application No. 61/431,376, filed on Jan. 10, 2011.

(51) Int. Cl.

| | | |
|---|---|---|
| *C12N 5/074* | (2010.01) | |
| *A61K 38/00* | (2006.01) | |
| *A61K 39/00* | (2006.01) | |
| *C07K 14/00* | (2006.01) | |
| *C07K 16/00* | (2006.01) | |
| *A61K 35/545* | (2015.01) | |

(52) U.S. Cl.
CPC ............ *C07K 16/00* (2013.01); *A61K 35/545* (2013.01); *A61K 38/00* (2013.01); *A61K 39/00* (2013.01); *C07K 14/00* (2013.01); *C12N 5/0696* (2013.01); *C07K 2317/14* (2013.01); *C07K 2317/41* (2013.01); *C12N 2510/02* (2013.01); *C12N 2517/04* (2013.01)

(58) Field of Classification Search
CPC ............ C12N 5/0696; C12N 2510/00; C12N 2510/02; C12N 2517/04; A61K 35/545; A61K 38/00; C07K 14/00; C07K 16/00; C07K 2317/14
See application file for complete search history.

(56) References Cited

U.S. PATENT DOCUMENTS

| | | | |
|---|---|---|---|
| 5,591,625 A | 1/1997 | Gerson | |
| 7,262,028 B2 | 8/2007 | Van Berkel | |
| 2001/0027237 A1 | 10/2001 | Mayes et al. | |
| 2004/0033217 A1 | 2/2004 | Vanguri | |
| 2008/0274125 A1* | 11/2008 | Guehenneux | 424/184.1 |
| 2009/0047263 A1* | 2/2009 | Yamanaka et al. | 424/93.21 |
| 2009/0053182 A1* | 2/2009 | Ichim | A61K 35/545 424/93.7 |
| 2009/0238802 A1 | 9/2009 | Vanguri | |
| 2009/0241206 A1 | 9/2009 | Sun et al. | |
| 2009/0257989 A1 | 10/2009 | Vanguri | |
| 2010/0255111 A1 | 10/2010 | Vanguri | |
| 2011/0027241 A1 | 2/2011 | Vanguri | |
| 2011/0263015 A1* | 10/2011 | D'Costa et al. | 435/366 |
| 2012/0122214 A1* | 5/2012 | Senju | 435/372 |

FOREIGN PATENT DOCUMENTS

| | | |
|---|---|---|
| WO | 9949015 A2 | 9/1999 |
| WO | 2010117464 A1 | 10/2010 |

OTHER PUBLICATIONS

Tsien, R.Y. The green fluorescent protein. Ann. Rev. Biochem., 1998, vol. 67, p. 509-544.*
Ho Ay—Immune tolerance therapy for haemophilia., Drugs. Sep. 2000.
Allez M,—The efficacy and safety of a third anti-TNF monoclonal antibody in Crohn's disease after failure of two other anti-TNF antibodies., Aliment Pharmacol Ther. Jan. 2010.
García-Patos Briones V—Long term efficacy and safety of etanercept in psoriasis., Actas Dermosifiliogr. May 2010.
Waters B, Lillicrap D.—The molecular mechanisms of immunomodulation and tolerance induction to factor VIII., J Thromb Haemost. Sep. 2009.
Qadura M—Immunoglobulin isotypes and functional anti-FVIII antibodies in response to FVIII treatment in Balb/c and C57BL/6 haemophilia A mice. Haemophilia. Mar. 2011.
Biggs R.—The absorption of human factor VIII neutralizing antibody by factor VIII., Br J Haematol. Feb. 1974.
Schellekens H—Immunogenicity of recombinant human proteins: causes and consequences., J Neurol. Jun. 2004.
Castelo-Soccio L—Long-term efficacy of biologics in dermatology., Dermatol Ther. Jan.-Feb. 2009.
Kanatsu-Shinohara M, Inoue K, Lee J, Yoshimoto M, Ogonuki N, Miki H, Baba S, Kato T, Kazuki—Generation of pluripotent stem cells from neonatal mouse testis . . . 7, 2004, Cell, vol. 119, pp. 1001-1012.
Guan, K.—Pluripotency of spermatogonial stem cells from adult mouse testis. 2006, Nature , vol. 440, pp. 1199-1203.
Kucia, M—Bone Marrow-Derived Very Small Embryonic-Like Stem Cells: Their Developmental Origin and Biological Significance. 2007, Developmental Dynamics , vol. 236, pp. 3309-3320.
Kobolak J—Generation of mouse embryonic stem cell lines from zona-free nuclear transfer embryos. 1, Feb. 2010, Cell Reprogram. , vol. 12, pp. 105-113.

(Continued)

*Primary Examiner* — Robert Landsman
*Assistant Examiner* — Bruce D Hissong
(74) *Attorney, Agent, or Firm* — Baumgartner Patent Law; Marc Baumgartner

(57) ABSTRACT

The invention provides a method for producing polypeptide protein products and nucleic acid products having reduced levels of antigenicity in an animal being treated with a biologic product. Somatic cells are isolated from an animal, transformed into pluripotent stem cells, transfected with a nucleic acid(s) of interest, and re-differentiated towards somatic cells known to be high level producers of the desired nucleic acid product. The invention can be used to derive a general cell line to treat populations, racial specific cell lines to treat ethnic groups, or patient specific cell lines to treat individuals. Additionally, the invention provides a method to allow induced pluripotent stem cells to be re-differentiated towards their somatic cell of origin so that the cells can be used to therapeutically treat an animal without resulting teratoma formation.

10 Claims, 1 Drawing Sheet

(56) References Cited

OTHER PUBLICATIONS

Byrnes, WM—The flawed scientific basis of the altered nuclear transfer-oocyte assisted reprogramming (ANT-OAR) proposal. 12, Dec. 2009, Genome Res. 2009, vol. 19, pp. 2193-2201.

Hu Q—Memory in induced pluripotent stem cells: reprogrammed human retinal-pigmented epithelial cells show tendency for spontaneous redifferentiation. 11, Nov. 2010, Stem Cells., vol. 28, pp. 1981-1991.

Wu D—Generation of induced pluripotent stem cells by reprogramming human fibroblasts with the stemgent human TF lentivirus set . . . 34, Dec. 2009, J Vis Exp., vol. 8, p. 1553.

Tat PA—The efficient generation of induced pluripotent stem (iPS) cells from adult mouse adipose tissue-derived and neural stem cells. 5, 2010, Cell Transplant., vol. 19, pp. 525-536.

Gong SP—Derivation of histocompatible stem cells from ovarian tissue. 5, Oct. 2010, J Reprod Dev., vol. 56, pp. 481-494.

Kim K—Epigenetic memory in induced pluripotent stem cells. et al. 7313, Sep. 2010, Nature. Sep. 16, 2010;467 (7313):285-90, vol. 467, pp. 285-290.

Polo JM—Cell type of origin influences the molecular and functional properties of mouse induced pluripotent stem cells. 8, Aug. 2010, Nat Biotechnol, vol. 28, pp. 848-855.

Sullivan GJ—Induced pluripotent stem cells: epigenetic memories and practical implications. 12, Dec. 2010, Mol Hum Reprod., vol. 16, pp. 880-885.

O'Malley J—New strategies to generate induced pluripotent stem cells. 5, Oct. 2009, Curr Opin Biotechnol., vol. 20, pp. 516-521.

Prentice, D.—Family Research Council. http://www.frcblog.com/2010/07/ips-cell-memory-and-stem-cell-confusion/. [Online] [Cited: Dec. 18, 2010.].

Takahashi K—Induction of pluripotent stem cells from mouse embryonic and adult fibroblast cultures by defined factors . . . 4, Aug. 2006, Cell. 2006, vol. 126, pp. 663-676.

Sommer CA—Induced pluripotent stem cell generation using a single lentiviral stem cell cassette. 3, Mar. 2009, Stem Cells., vol. 27, pp. 543-549.

Chang CW—Polycistronic lentiviral vector for "hit and run" reprogramming of adult skin fibroblasts to induced pluripotent stem cells. 5, May 2009, Stem Cells., vol. 27, pp. 1042-1049.

Balasubramanian S—Non cell-autonomous reprogramming of adult ocular progenitors: generation of pluripotent stem cells without exogenous transcription factors. 12, Dec. 2009, Stem Cells., vol. 27, pp. 3053-3062.

Ji Z—Reprogramming of 3' untranslated regions of mRNAs by alternative polyadenylation in generation of pluripotent stem cells from different cell types. 12, Dec. 2009, PLoS One., vol. 4, p. e8419.

Oliveri. RS—Epigenetic dedifferentiation of somatic cells into pluripotency: cellular alchemy in the age of regenerative medicine? 5, Sep. 2007, Regen Med., vol. 2, pp. 795-816.

Byrne, J.A.—Producing primate embryonic stem cells by somatic cell nuclear transfer. 2007, Nature, vol. 450, pp. 497-502.

Ratajczak—Very Small Embryonic-Like (VSEL) Stem Cells: Purification from Adult Organs, Characterization, and Biological Significance. 2008, Stem Cell Rev, vol. 4, pp. 89-99.

Park CH—In vitro and in vivo analyses of human embryonic stem cell-derived dopamine neurons . . . 2005, J Neurochem, vol. 92, p. 12.

Motomura Y—Embryonic Stem Cell-Derived Dendritic Cells Expressing Glypican-3, a Recently Identified Oncofetal Antigen, Induce Protective Immunity against Highly Metastatic Mouse Melanoma, B16-F10 . . . 4, 2006, Cancer Res, vol. 66, pp. 2414-2422.

Huss R—Contact- and growth factor-dependent survival in a canine marrow-derived stromal cell line . . . 9, May 1995, Blood., vol. 85, pp. 2414-2421.

http://www.healthtech.com/Conferences_Archive.aspx?id=96256. The BioPrecessing Summit 2009. [Online] 2009. [Cited: Dec. 19, 2010.].

Li J—Human antibodies for immunotherapy development generated via a human B cell hybridoma technology. 10, Mar 2006, Proc Natl Acad Sci, vol. 103, pp. 3557-3562.

Imai-Nishiya H—Double knockdown of alpha1,6-fucosyltransferase (FUT8) and GDP-mannose 4,6-dehydratase (GMD) in antibody-producing cells: a new strategy for generating fully non-fucosylated therapeutic antibodies with enhanced ADCC. Nov. 2007, BMC Biotechnol., vol. 7, pp. 84-97.

Merck. Varivax Summary for Basis of Approval. 1995. 93-095.

Hochuli, E—Applied Chemistry Division Commission on Biotechnology., Purification Techniques for Biological Products (Technical Report). 1, 1992, Pure & Appl. Chem, vol. 64, pp. 169-184.

Porro D—Production of recombinant proteins and metabolites in yeasts : When are these systems better than bacterial production systems? Appl Microbiol Biotechnol. Feb. 2011;89(4):939-48.

Chen SA—Incorporating significant amino acid pairs to identify O-linked glycosylation sites on transmembrane proteins and non-transmembrane proteins. Oct. 2010, BMC Bioinformatics, vol. 11, pp. 536-549 79.

Hausl C—Preventing restimulation of memory B cells in hemophilia A: a potential new strategy for the treatment of antibody-dependent immune disorders. 1, Jul. 2004, Blood. 2004, vol. 104, pp. 115-122.

Ingerslev, J.—Hemophilia. Strategies for the treatment of inhibitor patients. 10s, Oct. 2000, Haematologica., vol. 85, pp. 15-20.

Mersich C—Peptides derived from a secretory yeast library restore factor VIII activity in the presence of an inhibitory antibody. 1, Sep. 2007, Biotechnol Bioeng., vol. 98, pp. 12-21.

Salooja N—Use of a non-depleting anti-CD4 antibody to modulate the immune response to coagulation factors VIII and IX. 3, Sep. 2002, Br J Haematol., vol. 118, pp. 839-842.

Schramek D—Osteoclast differentiation factor Rankl controls development of progestin-driven mammary cancer. 7320, Nov. 2010, Nature., vol. 468, pp. 98-102.

Prosperini L—Natalizumab treatment in multiple sclerosis: the experience of S. Andrea MS Centre in Rome. Neurol Sci. Jan. 2011;31 Suppl 3:303-7].

Feng YQ—The human beta-globin locus control region can silence as well as activate gene expression. Mol Cell Biol. May 2005;25(10):3864-74.

Byrne JA—Generation of isogenic pluripotent stem cells. Hum Mol Genet. Apr. 15, 2008;17(R1):R37-41.

Eguizabal C—Complete meiosis from human induced pluripotent stem cells. Stem Cells. Aug. 2011;29(8):1186-95.

Feng Q—Hemangioblastic derivatives from human induced pluripotent stem cells exhibit limited expansion and early senescence. Stem Cells. Apr. 2010;28(4):704-12.

Vallier L—Signaling pathways controlling pluripotency and early cell fate decisions of human induced pluripotent stem cells. Stem Cells. Nov. 2009;27(11):2655-66.

Finckh A—Which subgroup of patients with rheumatoid arthritis benefits from switching to rituximab versus alternative anti-tumour necrosis factor (TNF) agents after previous failure of an anti-TNF agent? 2, Feb. 2010, Ann Rheum Dis., vol. 69, pp. 387-393.

Finckh A—Influence of anti-infliximab antibodies and residual infliximab concentrations on the occurrence of acquired drug resistance to infliximab in rheumatoid arthritis patients. 4, Jul. 2010, Joint Bone Spine., vol. 77, pp. 313-318.

Van Der Bijl AE—An open-label pilot study of the effectiveness of adalimumab in patients with rheumatoid arthritis and previous infliximab treatment: relationship to reasons for failure and anti-infliximab antibody status. 8, Aug. 2008, Clin Rheumatol., vol. 27, pp. 1021-1028.

Cassinotti A—Incidence and clinical significance of immunogenicity to infliximab in Crohn's disease: a critical systematic review. 8, Aug. 2009, Inflamm Bowel Dis., vol. 15, pp. 1264-1275.

Scheper W—The molecular mechanism of induced pluripotency: a two-stage switch. Stem Cell Rev. Sep. 2009;5 (3):204-23. Epub Jun. 24, 2009.

Ghosh Z—Persistent donor cell gene expression among human induced pluripotent stem cells contributes to differences with human embryonic stem cells. PLoS One. Feb. 1, 2010;5(2):e8975.

(56) References Cited

OTHER PUBLICATIONS

Fernández O—The efficacy of natalizumab in patients with multiple sclerosis according to level of disability: results of an observational study. Mult Scler. Feb. 2011;17(2):192-7.
Calabresi PA—The incidence and significance of anti-natalizumab antibodies: results from Affirm and Sentinel. 14, Oct. 2007, Neurology. , vol. 69, pp. 1391-1403.
Hyams JS—Natalizumab therapy for moderate to severe Crohn disease in adolescents. 2, Feb. 2007, J Pediatr Gastroenterol Nutr. , vol. 44, pp. 185-191.
Marchetto MC—Transcriptional signature and memory retention of human-induced pluripotent stem cells. PLoS One. Sep. 18, 2009;4(9):e7076.
Feng YQ—DNA methylation supports intrinsic epigenetic memory in mammalian cells. PLoS Genet. Apr. 2006;2(4):e65. Epub Apr. 28, 2006.
Mali P—Butyrate greatly enhances derivation of human induced pluripotent stem cells by promoting epigenetic remodeling and the expression of pluripotency-associated genes. Stem Cells. Apr. 2010;28(4):713-20.
Ohm JE—Cancer-related epigenome changes associated with reprogramming to induced pluripotent stem cells. Cancer Res. Oct. 1, 2010;70(19):7662-73. Epub Sep. 14, 2010.
Dolgin E.—Gene flaw found in induced stem cells. Nature. Apr. 1, 2010;464(7289):663.
Yamanaka S—Nuclear reprogramming to a pluripotent state by three approaches. Nature. Jun. 10, 2010;465 (7299):704-12.
Masip M—Reprogramming with defined factors: from induced pluripotency to induced transdifferentiation. Mol Hum Reprod. Nov. 2010;16(11):856-68. Epub Jul. 8, 2010. Review.
Laurent LC—Dynamic changes in the copy number of pluripotency and cell proliferation genes in human ESCs and iPSCs during reprogramming and time in culture. Cell Stem Cell. Jan. 7, 2011;8(1):106-18.
Kristeva MA.—Stem cells in light of a new concept for cell differentiation. Stem Cells Dev. Oct. 2008;17(5):849-52.
Liras A.—Future research and therapeutic applications of human stem cells: general, regulatory, and bioethical aspects. J Trans! Med. Dec. 10, 2010 ;8:131.
Lowry WE—Roadblocks en route to the clinical application of induced pluripotent stem cells. J Cell Sci. Mar. 1, 2010;123(Pt 5):643-51.
Hanna JH—Pluripotency and cellular reprogramming: facts, hypotheses, unresolved issues. Cell. Nov. 12, 2010;143(4):508-25. Review.
Stadtfeld M—Induced pluripotency: history, mechanisms, and applications. Genes Dev. Oct. 15, 2010;24 (20):2239-63. Review.
Eilertsen KJ—Targeting cellular memory to reprogram the epigenome, restore potential, and improve somatic cell nuclear transfer. Anim Reprod Sci. Mar. 2007;98(1-2):129-46. Epub Oct. 21, 2006. Review.
Giorgetti A—Generation of induced pluripotent stem cells from human cord blood cells with only two factors: Oct4 and Sox2. Nat Protoc. Apr. 2010;5(4):811-20. Epub Apr. 1, 2010.
Cho HJ—Induction of pluripotent stem cells from adult somatic cells by protein-based reprogramming without genetic manipulation. Blood. Jul. 22, 2010;116(3):386-95. Epub May 3, 2010.
Aasen T—Efficient and rapid generation of induced pluripotent stem cells from human keratinocytes. Nat Biotechnol. Nov. 2008;26(11):1276-84.
Zhao XY—Production of mice using iPS cells and tetraploid complementation. Nat Protoc. 2010;5(5):963-71.
Germain D.—Pathol Biol (Paris). [Induced pluripotent stem cells (iPS cells)]. Nov.-Dec. 2009;57(7-8):555-9.
Dan XU—A1 and YUPO MAA1, Phenotypic correction of murine hemophilia A using an iPS cell-based therapy. Proc Natl Acad Sci U S A. Jan. 20, 2009; 106(3): 808-813.
Moretti A—Patient-specific induced pluripotent stem-cell models for long-QT syndrome. N Engl J Med. Oct. 7, 2010;363(15):1397-409.
Hayashi EA—TLR4 promotes B cell maturation: independence and cooperation with B lymphocyte-activating factor. 9, May 2010, J Immunol., vol. 184, pp. 4662-4672.
Tateishi K—Generation of insulin-secreting islet-like clusters from human skin fibroblasts. 46, Nov. 2008, J Biol Chem. , vol. 283, pp. 31601-31607.
Shi Y—Inducing embryonic stem cells to differentiate into pancreatic beta cells by a novel three-step approach with activin A and all-trans retinoic acid. 5, May 2005, Stem Cells. , vol. 23, pp. 656-662.
Kristensen C—Alanine scanning mutagenesis of insulin . . . 20, May 1997, J Biol Chem., vol. 272, pp. 12978-12983.
Kjeldsen T—Engineering-enhanced protein secretory expression in yeast with application to insulin. 21, May 2002, J Biol Chem. , vol. 277, pp. 18245-18248.
Jeandidier N—Comparison of antigenicity of Hoechst 21PH insulin using either implantable intraperitoneal pump or subcutaneous external pump infusion in type 1 diabetic patients. 1, Jan. 2002, Diabetes Care. , vol. 25, pp. 84-88.
http://www.protocol-online.org/prot/Cell_Biology/Stem_Cells/Differentiation_of Stem_Cell/index.html. Protocol Online. [Online] [Cited: Dec 19, 2010.].
Zhao—Viable Fertile Mice Generated from Fully Pluripotent iPS Cells Derived from Adult Somatic Cells. Stem Cell Rev. Sep. 2010;6(3):390-7.

\* cited by examiner

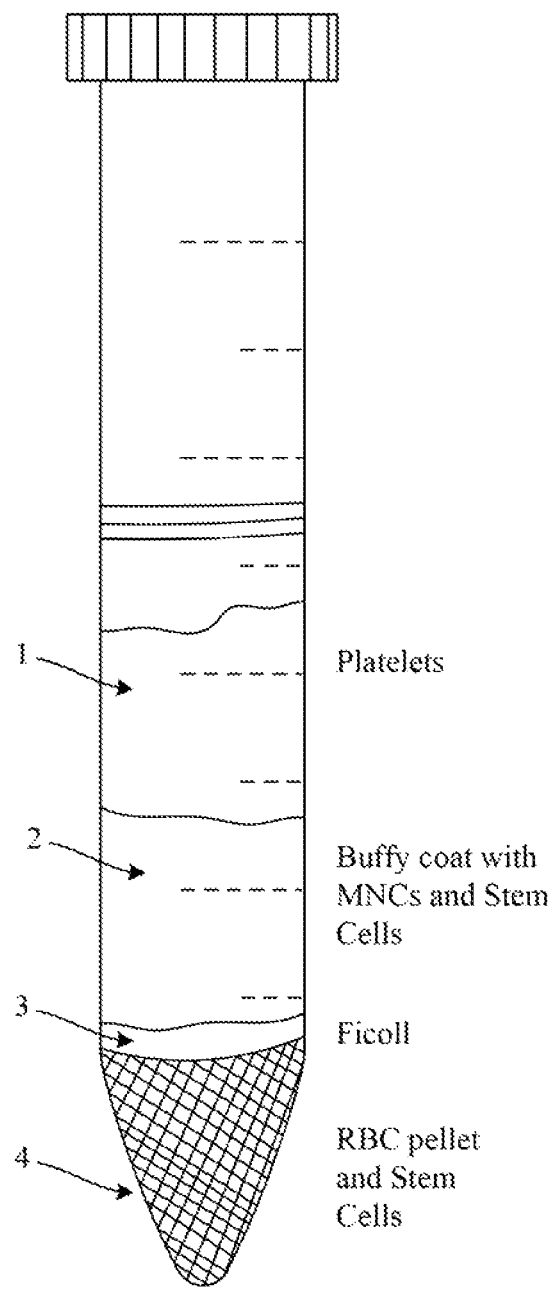
Layers resulting from gradient centrifugation of whole blood

PERSONALIZED PRODUCTION OF BIOLOGICS AND METHOD FOR REPROGRAMMING SOMATIC CELLS

CROSS-REFERENCE TO RELATED APPLICATIONS

This application claims priority to U.S. Provisional Patent Application Ser. No. 61/429,409 filed Jan. 3, 2011; U.S. Provisional Patent Application Ser. No. 61/431,376 filed Jan. 10, 2011. All of the foregoing applications are hereby incorporated by reference in their entirety.

BACKGROUND OF THE INVENTION

There are presently many recombinant polypeptides and proteins used therapeutically to treat a number of diseases. These recombinant polypeptides and proteins are all commercially manufactured using either primary, continuous non-human, or human diploid cell lines. For instance, some are manufactured using bacteria such as E. Coli, while others are manufactured using yeast or various ovarian cell lines of animal origin. Bacteria cannot be used for the manufacture of some polypeptides and proteins particularly when glycosylation patterns and other protein modifications are critical for biologic-receptor binding affinity, biologic activity, biodistribution or pharmacokinetics of the biologic or for recipient immune recognition. When glycosylation is a critical variable, the Chinese Hamster Ovary Cell is currently one of the most commonly used cell lines for biologic manufacture.

Unfortunately, the need to use a recombinant polypeptide or protein for long periods of time or for chronic therapy can result in the patient developing neutralizing antibodies to the product, making the patient less responsive or unresponsive to the drug. In some cases the patient can switch to another drug in the same class, such as with the variety of anti-TNF biologics, such as Enbrel, also known as Etanercept; Remicaide, also known as Infliximab; Certolizumab, and Humira, also known as D2E7, that are used to treat diseases such as rheumatoid arthritis, juvenile rheumatoid arthritis, psoriasis, psoriatic arthritis, ankylosing spondolytis, ulcerative colitis and Crohn's disease routinely. However, generation of neutralizing antibodies to one particular anti-TNF biologic in general predisposes the patient to ultimately generate neutralizing antibodies to another anti-TNF biologic product. In some instances, there are no alternative treatments for the patient, so this neutralizing antibody formation leaves the patient without treatment options. Even when there are appropriate treatment options, the pre-disposition to developing neutralizing antibodies to other drugs in the same class ultimately means that these patients may be left without treatment options.

Other biologic products that can be neutralized by human antibodies include: Nataliztimab, or Tysabri, an innovative therapy for multiple sclerosis, and Denosumab, a fully human monoclonal antibody to receptor activator of nuclear factor kappa-B ligand (RANKL), approved for the treatment of osteoporosis and chemotherapy-induced bone fracture, with potential use to treat breast cancer caused by HRT and hormonal contraceptives. Abatecept is a CTLA-4 fusion protein approved for use in rheumatoid arthritis patients who have become refractory to anti-TNF therapies. Although its use is too new to have evidence about Abatecept induced neutralizing antibodies, it also has the possibility that it may induce a human antibody neutralizing antibody reaction.

Other polypeptides and proteins besides the antibody and fusion protein based drugs have also been shown to elicit immune responses with long-term treatment. For instance, recombinant human erythropoietin elicits neutralizing antibody formation that reduces its efficacy and can lead to a rare aplasia syndrome. Also, the generation of antibodies to coagulation factor therapy for hemophiliacs is as high as 25-30% of the patients. This is a general problem with the coagulation factors. Recombinant interferon alpha 2a therapy for cancer and hepatitis B also are hampered by the generation of neutralizing antibodies to the treatment. Refractoriness to long-term growth hormone therapy for children with short stature is also problematic. There are reports of neutralizing antibody formation to some insulin products.

Other biologic drugs that have the potential to elicit neutralizing antibodies include whole blood, serum, plasma pools or other primary sources of biologic supply, for instance, human albumin, human Alpha1-Proteinase Inhibitor, human Antihemophilic Factor/von Willebrand Factor Complex, BabyBig Botulism Immune Globulin Intravenous, C1 Esterase Inhibitor, fibrin sealant, fibrinogen, Immune Globulin Intravenous, Immune Globulin Subcutaneous, Protein C Concentrate, Rho(D) Immune Globulin Intravenous, thrombin, von Willebrand Factor/Coagulation Factor VIII Complex.

Recombinant polypeptides and proteins elicit immune responses and neutralizing antibody generation based on multiple characteristics, including: the time frame of biologic treatment, the interval of repeat therapy, the amino acid composition of the biologic, and the modifications to the biologic such as glycosylation, methylation, nitrosylation, sialylation, phosphorylation, sulfation, prenylation, selenation, ubiquitinylation, vitamin-dependent modifications, protein binding associations, acylation, glycation, 3 dimensional configurations and supercoiling. Thus there is a need for methods of producing polypeptide protein products having reduced levels of antigenicity in an animal being treated with a biologic product.

The teachings of all of the references cited herein are incorporated in their entirety herein by reference.

DESCRIPTION OF THE INVENTION

The present invention fills this need by providing for methods to produce biologics such as polypeptides or proteins, nucleic acids, viruses and vaccines by transfecting or transforming synthetically produced pluripotent stem cells (spPSCs) or endogenous pluripotent stem cells (ePSC). These cells are derived from the species that is being treated and are transfected with vectors that express the desired biologic and induce expression of the biologic product by the transfected or transformed spPSC or ePSC.

The present invention further provides for a method for producing a recombinant polypeptide or protein comprising producing spPSCs from adult cells or isolating ePSCs of an animal and transfecting or transforming said spPSCs or ePSCs with a nucleic acid that encodes for said polypeptide or protein under conditions wherein the polypeptide or protein is expressed by said stem cell.

In an alternative embodiment of the present invention the spPSCs are produced or ePSCs are isolated from cells of the same ethnic group as that of the individual who is being administered the recombinant polypeptide or protein. Different ethnic groups may have varying glycosylation patterns and distinct polymorphisms from one group to another. Ethnic groups are those groups that have the same blood- or tissue-types. Thus, according to the present invention recombinant polypeptides and proteins are produced from spPSCs or ePSCs wherein the ePSCs are or spPSCs are produced from cells isolated from the same ethnic group as the individual being administered the polypeptide or protein. An individual will be administered a recombinant polypeptide or protein produced from an spPSC or ePSC wherein the spPSC is manufactured or the ePSC is isolated from a cell belonging to the ethnic group to which the individual belongs.

The present invention further provides for a method of administering a polypeptide or protein to an individual animal comprising producing spPSCs such as induced pluripotent stem cells (iPSCs) from said cells of said animal or isolating ePSCs and transfecting or transforming said spPSCs or ePSCs with a nucleic acid that encodes for said polypeptide or protein under conditions wherein the polypeptide or protein is expressed by said pluripotent stem cell, isolating said polypeptide or protein from said induced pluripotent stem cell and administering said isolated polypeptide or protein to said individual.

The present invention provides a method for personalized production of polypeptide or protein therapeutics thereby making spPSCs or ePSCs commercially viable and useful. The present invention relates to methods on how to make patient specific spPSCs or ePSCs to manufacture patient specific polypeptides or proteins to overcome issues of neutralizing antibody formation that occur commonly with polypeptides or protein for long term or chronic use. The patient can be any animal, preferably mammalian and more preferably human. The present invention also provides a method for producing nucleic acids or viruses comprised of transfecting or transforming spPSCs or ePSCs with a vector under conditions wherein the desired nucleic acid or virus is produced.

Furthermore, the present invention provides methods to derive a patient-specific and organ or cell-type specific cell line for the production of closely matched post-translationally modified biologics for therapeutic use. Patient specific stem cells can be derived using SCNT, induced reprogramming, parthenogenesis, or ANT-OAR reprogramming methods, or they can be isolated from the target patient. Pluripotent stem cells thus derived or isolated can be genetically modified using standard molecular biotechnology procedures to express the therapeutic of interest, for instance using insertional or episomal expression vectors or homologous recombination methods. The genetically modified cell line can be expanded in culture, and banked for periodic biologic production runs that would be scheduled based on the shelf-life of the produced biologic (EXAMPLE 2). Alternatively, the patient specific stem cell lines derived can be differentiated in culture towards a cell type that normally expresses the highest levels of the desired therapeutic protein and then used for biologic manufacture. Differentiation can be carried out for each production run, or could be done on large scale and the differentiated patient specific cell lines banked for subsequent production runs based on the shelf life of the therapeutic produced (EXAMPLE 3).

Additionally, since glycosylation patterns and other post-translational modifications are known to differ among tissues and cell types, patient specific stem cell lines can be prepared from adult or somatic cells isolated from the organ or from among the cell-type that endogenously expresses the biologic. As an example, SCNT, PGA, ANT-OAR or reprogramming techniques can then be applied to derive a pluripotent cell line for biologic production. Pluripotent stem cells thus derived or isolated can be genetically modified using standard molecular biotechnology procedures to express the therapeutic of interest. The genetically modified cell line can be expanded in culture, and banked for periodic biologic production runs, that would be scheduled based on the shelf-life of the produced biologic (See Example 4). Taking further advantage of the 'memory' properties of reprogrammed cells (iPS cells), patient and tissue or cell-type specific iPS cells can be induced to differentiate back towards their cell-type of origin to more fully create a cell line capable of endogenous post-translational modification. The iPS cells may be genetically modified to express the therapeutic of interest prior to re-differentiation towards the original isolated cell-type or after re-differentiation towards the original cell type (See Example 5).

For instance, growth hormone is normally most highly produced by somatotrophic cells in the anterior pituitary, and is also highly expressed in cells within the placenta (trophoblasts) and the tongue and vulva or anal skin. Factor VIII protein expression is high in tubule cells in the kidneys, and is moderately expressed by multiple tissues and cell types, according to the Human Protein Atlas. Antibodies are typically produced by B cells which mature in germinal centers of the spleen and other lymphoid organs. Therapeutic production of antibodies with high levels of antibody-dependent cell-mediated cytoxicity (ADCC) are determined by the level of GDP-D-mannose-4,6-dehydratase (GMD) that can place N-acetylglucosamine (GlcNac) at the bisecting position of IgG1 subtype antibodies present in the manufacturing cell line (*J Biol Chem.*, Vol. 273, pp. 14582-14587, 1998 and *BMC Biotechnol.*, 7:84-97 (2007). Production of antibodies with high ADCC activity is not always optimal using the CHO manufacturing cell line (*J Biol Chem.* 278: 3466-3473, 2003). The present invention provides novel mammalian cell lines for optimal ADCC activity of manufactured antibodies, fusion proteins and cell cytotoxic biologics.

Transcription factors known to be associated with high levels of biologic production can be co-transfected with the gene of interest to optimize expression levels from the patient specific cell line. For instance, high levels of Pit-1 expression may lead to high prolactin expression in a cell type while blocking or preventing growth hormone expression (*Genes Dev*, 3: 946-958 1989).

Monoclonal antibody production can be enhanced by optimizing the gene codon using systems such as those developed by Sino Biological Inc, Peoples Republic of China, morphogenics (*Proc Natl Acad Sci*, 103: 3557-3562, 2006), or other standard biotechnology methods.

Production of Synthetically Produced-Pluripotent Stem Cells

Any type of synthetically produced pluripotent stem cell can be used to produce the personalized biologics of the present invention. The two main categories are induced or reprogrammed Pluripotent Stem Cells (iPSCs) and stem cells produced by nuclear transfer (SCNT), ANT-OAR and parthenogenesis.

Somatic cell nuclear transfer (SCNT) is a technique wherein an enucleated egg is injected with the nucleus of an adult somatic cell and implanted in a prepared recipient uterus with resulting live births that yield complete nuclear genetic clones. Additionally, pluripotent stem cells have been derived in culture from SCNT methods (*Cell Reprogram.* 12:105-113, 2010 and *Genome Res.*, 19: 2193-2201, 2009).

Altered nuclear transfer, oocyte assisted reprogramming (ANT-OAR) is a technique similar to SCNT, however, the donor nucleus is genetically altered prior to injection into the recipient egg such that the ANT-oocyte is prevented from differentiating and forming a complete organism (*Genome Res.* 19: 2193-2201, 2009).

Parthenogenesis (PGA) is also used to generate pluripotent stem cells, using techniques such as zona-free nuclear transfer, parthenogenetic activation; and cloning techniques such as SCNT and parthenogenesis (PGA) have also been used to generate reprogrammed pluripotent stem cells (*Cell Reprogram.*, 12: 105-113, 2010 and *Nature,* 450:497-502 2007).

These pluripotent stem cells can be maintained for somewhat long term indefinite periods in culture, making them a potential source for biologic manufacturing such as for recombinant proteins, DNA, and viruses.

Induced or Reprogrammed spPSC

Induced Pluripotent Stem Cells are similar to natural pluripotent stem cells, such as embryonic stem (ES) cells, in many respects, such as the expression of certain stem cell genes and proteins, chromatin methylation patterns, doubling time, embryoid body formation, teratoma formation, viable chimera formation, and potency and differentiability.

Induced pluripotent, stem cells, commonly abbreviated as iPS cells or iPSCs are a type of pluripotent stem cell artificially derived from a non-pluripotent cell, typically an adult somatic cell, by inducing a "forced" expression of specific genes (*Nature Reports Stem Cells.* 2007).

Induced Pluripotent Stem Cells (iPSCs) are produced by transfection of certain stem-cell associated genes into non-pluripotent cells. Induced pluripotent stem cells are typically derived by transfection of certain stem cell-associated genes into non-pluripotent cells such as adult fibroblasts. Transfection is typically achieved through viral vectors, such as retroviruses or retrotransposons. Transfected genes include the master transcriptional regulators Oct-3/4 (Pou5f1) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection.

Embryonic stem cell derived fibroblasts and adult fibroblasts and other cells have been reprogrammed to a pluripotent state by fusion with embryonic stem cells (Cell. 126:652-655, 2006 and Stem Cell Rev, 2: 331-340, 2006), by the addition of 4 genes using retroviral transfection techniques (Cell. 126:663-676, 2006), by a single cassette or bicistronic lentiviral transfection methods [Stem Cells., 27:543-549, 2009, and Stem Cells., 27:1042-1049, 2009), and by endogenous stimulation of pluripotency required transcription factors (Stem Cells., 27:3053-3062, 2009). Induction or maintenance of pluripotency could also be achieved by modifying methylation or polyadenylation status of the genome (PLoS One., 4:e8419, 2009), by microRNAs (Dev Biol., 344:16-25, 2010), small molecule activators of required transcription factors, epigenetic reprogramming (Regen Med., 2:795-816, 2007), by protein-based reprogramming, (Blood 116: 386-395, 2010) by addition of culture supernatant or cell extracts from pluripotent cells in culture, and by chemical or radiation or other means of genetic mutation to reactivate pluripotency genes, and by addition of growth factors or cytokines or cellular signaling moieties that induce or maintain endogenous pluripotent states.

The use of retroviruses to re-program cells to pluripotent states presents dangers that recall the gene therapy trials for immune deficiency. Excision techniques such as Cre-lox have been used to eliminate the retrovirus after successful reprogramming and piggyBac transposon methods totally eliminate the need for retroviruses (*Curr Opin Biotechnol.,* 20:516-521, 2009).

Human iPSCs have been produced by transforming human fibroblasts into pluripotent stem cells using four pivotal genes: Oct3/4, Sox2, Klf4, and c-Myc with a retroviral system. Human iPSCs have also been produced using OCT4, SOX2, NANOG, and a different gene LIN28 using a lentiviral system. Adenovirus has also been used to transport the requisite four genes into the DNA of skin and liver cells of mice, resulting in cells identical to embryonic stem cells (*Science* 322(5903):945-949, 2008). Reprogramming of adult cell to iPSCs can also be accomplished via plasmid without any virus transfection system at all (*Science* 322 (5903):949-953, 2008). iPSCs have been produced using the piggy bac transposon system, mini circle technology, protein stimulated or conditioned media stimulated reprogramming.

The generation of iPS cells is crucially dependent on the genes used for the induction. Oct-3/4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (C-myc, L-myc, and N-myc), Nanog, and LIN28, have been identified to increase the induction efficiency.

Oct-3/4 (Pou5f1) (cDNA available from Bioclone, San Diego Calif.) (*Nucleic Acids Res.* 20 (17): 4613-20, 1992): Oct-3/4 is one of the family of octamer ("Oct") transcription factors, and plays a crucial role in maintaining pluripotency. The absence of Oct-3/4 in Oct-3/4$^+$ cells, such as blastomeres and embryonic stem cells, leads to spontaneous trophoblast differentiation, and presence of Oct-3/4 thus gives rise to the pluripotency and differentiation potential of embryonic stem cells. Various other genes in the "Oct" family, including Oct-3/4's close relatives, Oct1 and Oct6, fail to elicit induction, thus demonstrating the exclusiveness of Oct-3/4 to the induction process.

Sox family: The Sox family of genes is associated with maintaining pluripotency similar to Oct-3/4, although it is associated with multipotent and unipotent stem cells in contrast with Oct-3/4, which is exclusively expressed in pluripotent stem cells (*Dev Biol.* 227 (2): 239-55, 2000). While Sox2 (cDNA available from Bioclone, San Diego, Calif.) was the initial gene used for induction (*Mamm. Genome* 5 (10): 640-642, 1995), other genes in the Sox family have been found to work as well in the induction process. Sox1 (cDNA available from Bioclone, Inc., San Diego, Calif.) yields iPS cells with a similar efficiency as Sox2, and genes Sox3 (human cDNA available from Bioclone, Inc., San Diego, Calif.), Sox15, and Sox18 also generate iPS cells, although with decreased efficiency.

Klf family: Klf4 of the Klf family of genes is a factor for the generation of mouse iPS cells. Klf2 (cDNA available from Bioclone, Inc., San Diego, Calif.) and Klf4 (cDNA available from Bioclone, Inc., San Diego, Calif.) are factors capable of generating iPS cells, and related genes Klf1 (cDNA available from Bioclone, Inc., San Diego, Calif.) and Klf5 (cDNA available from Bioclone, Inc., San Diego, Calif.) did as well, although with reduced efficiency.

Myc family: The Myc family of genes are proto-oncogenes implicated in cancer. C-myc (cDNA available from Bioclone, Inc., San Diego, Calif.) is a factor implicated in the generation of mouse iPS cells. However, c-myc may be unnecessary for generation of human iPS cells. Usage of the "myc" family of genes in induction of iPS cells is troubling for the eventuality of iPS cells as clinical therapies, as 25% of mice transplanted with c-myc-induced iPS cells developed lethal teratomas. N-myc (cDNA available from Bioclone, Inc., San Diego, Calif.) and L-myc have been identified to induce instead of c-myc with similar efficiency.

Nanog: (cDNA available from Bioclone, Inc., San Diego, Calif.) In embryonic stem cells, Nanog, along with Oct-3/4 and Sox2, is necessary in promoting pluripotency (*Cell* 113 (5): 643-55, 2003).

LIN28: (cDNA available from Bioclone, Inc., San Diego, Calif.) LIN28 is an mRNA binding protein expressed in embryonic stem cells and embryonic carcinoma cells associated with differentiation and proliferation (*Dev Biol* 258 (2): 432-42, 2003).

Identity of Synthetically Produced-Pluripotent Stem Cells

The generated spPSCs are remarkably similar to naturally isolated pluripotent stem cells (such as mouse and human embryonic stem cells (ESCs), mESCs and hESCs, respectively) in the following respects, thus confirming the identity, authenticity, and pluripotency of spPSCs to naturally isolated pluripotent stem cells:

Cellular Biological Properties:

Morphology: iPSCs are morphologically similar to ESCs. Each cell has round shape, large nucleolus and scant cytoplasm. Colonies of iPSCs are also similar to that of ESCs. Human iPSCs form sharp-edged, flat, tightly-packed colonies similar to hESCs and mouse iPSCs form the colonies similar to mESCs, less flat and more aggregated colonies than that of hESCs.

Growth properties: Doubling time and mitotic activity are cornerstones of ESCs, as stem cells must self-renew as part of their definition. iPSCs are mitotically active, actively self-renewing, proliferating, and dividing at a rate equal to ESCs.

Stem cell markers: iPSCs express the same cell surface antigenic markers expressed on ESCs. Human iPSCs express the markers specific to hESC, including SSEA-3, SSEA-4, TRA-1-60, TRA-1-81, TRA-2-49/6E, and Nanog. Mouse iPSCs expressed SSEA-1 but not SSEA-3.nor SSEA-4, similarly to mESCs.

Stem Cell Genes: iPSCs express genes expressed in undifferentiated ESCs, including Oct-3/4, Sox2, Nanog, GDF3, REX1, FGF4, ESG1, DPPA2, DPPA4, and hTERT.

Telomerase activity: Telomerases are necessary to sustain cell division unrestricted by the Hayflick limit of ~50 cell divisions. hESCs express high telomerase activity to Sustain self-renewal and proliferation, and iPSCs also demonstrate high telomerase activity and express hTERT (human telomerase reverse transcriptase), a necessary component in the telomerase protein complex.

Pluripotency: iPSCs are capable of differentiation in a fashion similar to ESCs into fully differentiated tissues:

Neural differentiation: iPSCs can differentiate into neurons, expressing βIII-tubulin, tyrosine hydroxylase, AADC, DAT, ChAT, LMX1B, and MAP2. The presence of catecholamine-associated enzymes may indicate that iPSCs, like hESCs, may be differentiable into dopaminergic neurons. Stem cell-associated genes are downregulated after differentiation.

Cardiac differentiation: iPSCs can differentiate into cardiomyocytes that spontaneously begin beating. Cardiomyocytes expressed TnTc, MEF2C, MYL2A, MYHCβ, and NKX2.5. Stem cell-associated genes were downregulated after differentiation.

Teratoma formation: iPSCs injected into immunodeficient mice spontaneously form teratomas after nine weeks. Teratomas are tumors of multiple lineages containing tissue derived from the three germ layers endoderm, mesoderm and ectoderm; this is unlike other tumors, which typically are of only one cell type. Teratoma formation is a landmark test for pluripotency.

Embryoid body: hESCs in culture spontaneously form ball-like embryo-like structures termed "embryoid bodies", which consist of a core of mitotically active and differentiating hESCs and a periphery of fully differentiated cells from all three germ layers. iPSCs also form embryoid bodies and have peripheral differentiated cells.

Tetraploid complementation: iPS cells from mouse fetal fibroblasts injected into tetraploid blastocysts (which themselves can only form extra-embryonic tissues) can form whole, non-chimeric, fertile mice, although with low success rate. The tetraploid complementation assay is a technique in biology in which cells of two mammalian embryos are combined to form a new embryo. It is used to construct genetically modified organisms, to study the consequences of certain mutations on embryonal development, and in the study of pluripotent stem cells.

Induced pluripotent stem cells (iPS) have been generated from gut mesentery cells (*Cell Reprogram.*, 12:237-247, 2010), retinal pigmented epithelial cells (*Stem Cells.*, 28:1981-1991, 2010), amnion cells (*Differentiation.*, 80:123-129, 2010), fibroblasts (*J Vis Exp.*, 8:1553, 2009), adult neural cells (*Nature.*, Vol. 454, pp. 646-650, 2008), dental pulp (*J Dent Res, Vol.* 89, pp. 773-778, 2010), adipose cells (*Cell Transplant.*, 19:525-536, 2010), ovarian (*J Reprod Dev.*, 56:481-494, 2010), and many other cells from embryonic, fetal and adult sources. iPS cells can be produced from any cell type, theoretically, although all 220 cell types of the body have not yet been systematically investigated. Several recent studies have demonstrated that iPS cells retain a 'memory' for their cell type of origin. This translates to a preference of iPS cells to re-differentiate in culture, sometimes spontaneously, most readily towards their cell type of origin.

Isolation of Endogenous Stem Cells

Stem cells, including endogenous pluripotent stem cells (ePSCs), can be characterized and isolated by specific antigens expressed on their surface. Pluripotent stem cells can be characterized by the expression of stage-specific embryonic antigen (SSEA), the transcription factors Oct4 and Nanog and other markers, among other methods. The primary type of endogenous pluripotent stem cell that has been isolated to date is the very small embryonic-like (VSEL) stem cells.

VSELs are small (3-5 micron diameter in the mouse and 3-7 micron diameter for human), with high nuclear to cytoplasmic ratio. VSELs are positive for SSEA1, Oct4, Nanog, Rex1 and other pluripotent stem cell markers, and for CD133, CD34, AP, cMet, LIF-R, and CXCR4. (J Am Coll Cardiol 53(1):10-20, 2009; Stem Cell Rev 4:89-99, 2008). They are negative for CD45. VSELs are smaller than HSCs (3-6 vs. 6-8 μm) and have higher nucleus/cytoplasm ratio. The VSEL nucleus is large, contains open-type chromatin and is surrounded by the narrow rim of cytoplasm with numerous mitochondria. Therefore, their morphology is consistent with primitive PSC.

The absolute numbers of circulating VSELs in PB are exceptionally low (1 to 2 cells in 1 mL of blood under steady-state conditions) and thus special flow cytometric protocols have to be applied for their identification and isolation. Phenotypic markers used to identify VSELs include negative expression of CD45 (mouse and human), positive expression of Sca-1 (mouse), CXCR4, CD133 and CD34 (mouse and human), positive for progenitor stem cell markers (that is, Oct-4, Nanog and SSEA) and express several markers characteristic of epiblast/germ line stem cells.

Employing only fluorescence activated cell sorter isolation of VSELs, sorting of all the VSELs present in 100 mL of UCB can be complete within 4 working days. A more efficient and economic three-step isolation protocol allows recovery of 60% of the initial number of Lin−/CD45−/CD133♭ UCB− VSELs. The protocol includes lysis of erythrocytes in a hypotonic ammonium chloride solution, CD133♭ cell selection by immunomagnetic beads and sorting of Lin−/CD45−/CD133♭ cells by FACS with size-marker bead controls. The isolated cells are highly enriched for an Oct-4♭ and SSEA-4♭ population of small, highly primitive Lin−/CD45−/CD133♭ cells.

Another method for sorting of VSELs is based on the presence of several surface markers and the diameter of the cells. Briefly, the initial step is the lysis of red blood cells to obtain the fraction of nucleated cells. Erythrocyte lysis buffer is used instead of Ficoll centrifugation because the latter approach might deplete the population of very small cells. Subsequently, cells are stained with antibodies against Sca-1 (murine VSELs) or CD133 (human VSELs), panhematopoietic antigen (CD45), hematopoietic lineages markers (lin), and CXCR4 and sorted using a multiparameter, live sterile cell sorting systems (MoFlo, Beckman Coulter; FACSAria, Beckton Dickinson). This method uses "extended lymphocyte gate" to include events with diameter 2-10 μm, including approximately 95% of VSELs.

Endogenous stem cells may be contained within the mononuclear cell fraction from bone marrow, whole blood, umbilical cord blood, adipose tissue or other sources, or they may be purified by selection for CD34, CD133, CD105, CD117, SSEA1-4, dye exclusion or other specific stem cell antigens. Stem cells can be isolated from whole blood, bone marrow, umbilical cord blood, adipose tissue, tissue scrapings from the olfactory mucosa and other stem cell sources that can be dissociated into single cell suspensions, such as umbilical cord tissue, by density gradient centrifugation using Ficoll-Hypaque or other commercially available gradients. Stem cells can be recovered from the mononuclear cell fraction resulting from such procedures. Alternatively, stem cells can be found within other fractions after density gradient centrifugation (*Stem Cells Dev.* 2011 [Epub ahead of print].) For instance, umbilical cord blood can be diluted 1:1 in PBS, carefully overlaid onto Histopaque 1077 (Sigma) and centrifuged at 1500 rpms at room temperature for 30 minutes. The resulting layers as depicted can be further processed for stem cell isolation. Layer 1 is the platelet layer, layer 2 is the buffy coat containing mononuclear cells, layer 3 is the Ficoll layer, and layer 4 is the red blood cell pellet layer, which also contains VSELs. Layers 1, 2, and 3 can be collected, diluted with appropriate media such as DM EM F12 with or without FBS and centrifuged again to obtain the cell pellet. Layer 4 can be diluted with appropriate media such as DMEM F12 and centrifuged at 800 rpm for 15 minutes at room temperature in a standard benchtop centrifuge. Stem cells can be recovered predominantly from layer 2 (Buffy coat) and layer 4 (RBC pellet), following the types of flow cytometric methods outlined above. FIG. 1 shows a typical view of layers resulting from gradient centrifugation of whole blood. 1 shows the platelets; 2 the buffy coat with MNCs and stem cells; 3 the ficoll; and 4 the RBC pellet and stem cells.

Additionally, since glycosylation patterns and other post-translational modifications may differ among tissues and cell types, patient specific stem cell lines can be prepared from adult or somatic cells isolated from the organ or from among the cell-type that endogenously expresses the biologic. See Rajpert-De Meyts E, et al. "Changes in the profile of simple mucin-type O-glycans and polypeptide GalNAc-transferases in human testis and testicular neoplasms are associated with germ cell maturation and tumour differentiation"., *Virchows Arch, Vol.* 451:805-814 (2007). See Pevalova M., et al. "Post-translational modifications of tau protein". *Bratisl Lek Listy*, 107:346-353 (2006).

DETAILED DESCRIPTION OF THE PREFERRED EMBODIMENT

Production of Immortalized spPSCs and ePSCs

In a preferred embodiment of the present invention the spPSCs and ePSCs are immortalized preferably through non-viral induction of the large T-antigen typically using the polyomavirus simian virus 40 (SV40). See Rose, M. R. et al., (1983). "Expression of the Large T Protein of Polyoma Virus Promotes the Establishment in Culture of "Normal" Rodent Fibroblast Cell Lines". *PNAS* 80: 4354-4358 (1983); and Hofmann, M. C. et al. "Immortalization of germ cells and somatic testicular cells using the SV40 large T antigen" *Experimental Cell Research*, 201:417-435 (1992).

Overview of an Embodiment Using Synthetically Produced, Preferably, Induced Pluripotent Stem Cells or More Preferably Isolated Endogenous Pluripotent Stem Cells In a preferred embodiment:
1. Endogenous pluripotent stem cells are isolated;
2. The ePSC are immortalized;
3. The immortalized ePSC are transfected with the gene, virus or nucleic acids of interest using non-viral technology;
4. The transfected, immortalized ePSC are then induced to differentiate into a germ line cell, preferably an ovary cell, so as to be able to express nucleic acid product in a more efficient manner;
5. The differentiated cell can now be induced to express the nucleic acid product of interest from the previously transfected vector containing the nucleic acids of interest.

In another preferred embodiment:
1. Somatic cells are isolated;
2. The somatic cells are transformed into induced pluripotent stem cells (iPS cells);
3. The iPS cells are immortalized;
4. The immortalized iPS cells are transfected with a vector containing the gene, virus or nucleic acids of interest;
5. The transfected, immortalized iPS cells are then induced to re-differentiate into a somatic cell so as to be able to express protein in a more efficient manner;
6. The re-differentiated cell can now be induced to express the protein of interested from the previously transfected vector containing the gene of interest.

In an even more preferred embodiment:
1. Endogenous pluripotent stem cells are isolated;
2. The immortal ePSC are transfected with the gene, virus or nucleic acids of interest using non-viral technology;
3. The transfected, immortalized ePSC are then induced to differentiate into a germ line cell, preferably an ovary cell, so as to be able to express nucleic acid product in a more efficient manner;
4. The differentiated cell can now be induced to express the nucleic acid product of interest from the previously transfected vector containing the nucleic acids of interest.

Methods to accomplish the preferred embodiments of this invention are well known to those skilled in the art.

In alternative embodiments the ePSC or spPSC can be transfected with the vector containing the nucleic acids of interest prior to being immortalized. See Du C. et al. "Generation of Variable and Fixed Length siRNA from a novel siRNA Expression Vector", *Biomed. & Biophys. Res. Comm.* 345:99-105 (2006); York Zhu, U.S. patent application Ser. No. 12/313,554 filed on Nov. 21, 2008. Or the ePSC or spPSC cells can be induced to re-differentiate and then the cells can be immortalized and the immortalized, re-differentiated cells can be transfected with a vector containing the nucleic acids of interest. Another possibility is the ePSC or spPSC cells. can be induced to re-differentiate, the re-differentiated cells can be transfected with the nucleic acids of interest and the re-differentiated, transfected cells can be immortalized.

It is preferable that the ePSC or spPSC cells be expanded in culture prior to re-differentiation, preferably in a cell culture medium containing autologous human serum and stem cell factor or leukemia inhibitory factor.

The polypeptide or protein that is produced can be any polypeptide or protein. Of particular interest are the polypeptides or proteins selected from the group consisting of erythropoietin, factor VIII, factor IX, thrombin, an antibody or antibody fragment, alpha interferon, interferon alpha 2A and 2B (See U.S. Pat. Nos. 4,810,645 and 4,874,702), beta interferon (See U.S. Pat. No. 4,738,931), consensus interferon (See U.S. Pat. No. 5,661,009), growth hormone, antihemophilic factor, G-CSF, GM-CSF, a soluble receptor, fusion proteins such as the fusion of a soluble receptor to the constant region of an immunoglobulin (Ig) (See U.S. Pat. No. 5,155,027), TGF-β, bone morphogenic proteins (BMP), TGFα, interleukin 2, β-glucocerebrosidase or an analogue thereof, alpha 1-proteinase inhibitor, fibrin, fibrinogen, von Willebrand factor, imiglucerase, agalsidase beta, laronidase, alglucosidase alpha, alglucosidase alpha, thyrotropin alpha, and thymosin alpha.

Any antibody or antibody fragment can be produced according to the process of the present invention. Of particular interest are those antibodies or antibody fragments that bind to a target, wherein said target is selected from the group consisting of a tumor necrosis factor (TNF) molecule, a growth factor receptor, a vascular endothelial growth factor (VEGF) molecule, interleukin 1, interleukin 4, interleukin 6, interleukin 11, interleukin 12, gamma interferon, Receptor activator of nuclear factor kappa-B ligand (RANKL) and Blys.

Induction of Differentiation of Stem Cells

To optimize production of the protein of interest, the transfected ePSC or spPSC cells should be induced to differentiate into a somatic cell.

In an alternative embodiment the population of the ePSC or spPSC cells could be expanded and differentiation can be induced and the differentiated cells could then be transfected with the nucleic acid of interest. Stem cells can be induced to differentiate towards somatic cell types in culture by the addition of various growth factors to the culture (*Blood.*, 85:2414-2421, 1995), by altering nutrients in the culture media, by manipulating culture conditions such as oxygen tension, (*BMC Cell Biol.*, 11:94, 2010) or temperature, or by culturing the stem cells on various extracellular matrices, among other methods as are known to those in the field of cellular biology and cell differentiation. For instance, retinoic acid, TGF-β, bone morphogenic proteins (BMP), ascorbic acid, and beta-glycerophosphate lead to production of osteoblasts; indomethacin, IBMX (3-isobutyl-1-methylxanthine), insulin, and triiodothyronine (T3) lead to production of adipocytes; αFGF, βFGF, vitamin D3, TNF-β and retinoic acid lead to production of myocytes (*CARDIAC-DERIVED STEM CELLS.* (WO/1999/049015) March 1998). Germ cells have been generated from pluripotent stem cells using monolayer culture, the formation of embryoid bodies (EBs), co-aggregation with BMP4-producing cells, and the use of testicular or ovarian cell-conditioned medium, or EB formation with recombinant human bone morphogenetic proteins (BMPs) (*PLoS One.* 2009; 4(4):e5338). Germ cell marker genes include PR domain containing 1, with ZNF domain (PRDM1, also known as BLIMP1), PR domain containing 14 (PRDM14), protein arginine methyltransferase 5 (PRMT5), DPPA3, IFITM3, GDF3, c-KIT, chemokine (C-X-C motif) receptor 4 (CXCR4), NANOS1-3, DAZL, VASA, PIWI family genes (PIWIL1 and PIWIL2, known as HIWI and HILI in humans, respectively), Mut-L Homologue-1 (MLH1), synaptonemal complex protein 1 (SCP1), and SCP3. The resulting germ cell lines can be genetically modified to express gene or protein products of interest similarly to the use of Chinese Hamster Ovary (CHO) cells and other currently used manufacturing cells lines. Differentiation strategies to obtain various somatic cell lines from stem cells at various stages are well known to those in the field of stem cell biology.

Transcription factors known to be associated with high levels of biologic production can be co-transfected with the gene of interest to optimize expression levels from the patient specific cell line. For instance, high levels of Pit-1 expression may lead to high prolactin expression in a cell type while blocking or preventing growth hormone expression (*Genes Dev,* 3:946-958, 1989).

Monoclonal antibody production can be enhanced by optimizing the gene codon using systems such as those developed by Sino Biological Inc, morphogenics, or other standard biotechnology methods.

According to the present invention recombinant polypeptides and proteins are produced in ePSCs and spPSCs wherein the spPSCs and ePSCs are produced or isolated from cells of a specific breed or ethnic group due to the fact that some breeds or ethnic groups of a specific species of animal have different glycosylation patterns in the polypeptides or proteins produced by the specific breed or ethnic group. According to the present invention an ethnic group is a group of people whose members identify with each other, through a common heritage, often consisting of a common ancestry or endogamy (the practice of marrying within a specific group for example Ashkenazi Jews). In general it is a highly biologically self-perpetuating group. Examples of ethnic groups that may have different glycosylation patterns in the polypeptides and proteins are illustrated in Levinson, David (1998), *Ethnic Groups Worldwide: A Ready Reference Handbook*, Greenwood Publishing Group.

Method and System for Stem Cell Therapy

The present invention also includes a method for promoting stem cell therapy without formation of teratomas. The present invention teaches how to advantageously utilize the observed 'memory' of reprogrammed somatic cells herein called synthetically produced Pluripotent Stem Cells (spPSC) defined above, for greater therapeutic benefit. The memory of spPSCs, which confers a preference to re-differentiate towards the cell type of origin prior to reprogramming, provides a means to enhance the safety and therapeutic utility of spPSCs for regenerative medicine.

General Steps

The present invention involves
1. Isolation of somatic cells of interest especially somatic cells that one wishes to regenerate;
2. Transformation of the somatic cells into synthetically produced Pluripotent Stem Cells (spPSCs), especially induced Pluripotent Stem Cells (iPSCs) as described above;
3. Expansion of the population of spPSCs wherein the spPSCs maintain the intrinsic epigenetic memory of the somatic cell;
4. Re-differentiation of the spPSCs in culture to re-differentiated somatic cells having the original somatic cell type; and
5. Administration or delivery of the re-differentiated somatic cells into the area of the body where the cell-type is desired.

Several recent studies have demonstrated that spPSCs cells retain a 'memory' for their cell type of origin (*Stem Cells*. 28: 1981-1991, 2010), (*Nature*, 467(7313):285-90, 2010), (*Nat Biotechnol*, 28: 848-855, 2010) and (*Mol Hum Reprod.*, 16:880-885, 2010). This translates to a preference of spPSCs to re-differentiate in. Culture, sometimes spontaneously, most readily towards their cell type of origin. Scientists and clinician scientists have focused with a tunnel determination on generating pluripotent stem cells that might be useful for clinical therapy, for drug discovery, for disease modeling or for toxicity screening (*Curr Opin Biotechnol.*, 20: 516-521, 2009), missing the therapeutic advantage that the memory aspect of pluripotent stem cells provides for safe human therapy. Indeed, the scientists who published data regarding the 'memory' aspects of reprogrammed pluripotent stem cells have focused on the limitations that this property of spPSCs cells create for therapy, and have missed the significance of this property for providing therapeutic utility of these cells The memory aspect of spPSCs has been observed from somatic cells of multiple origins. For instance, primary fetal retinal epithelial cells were reprogrammed into iPSCs using lentiviral expression of OCT4, SOX2, LIN28, and Nanog (*Stem Cells*. 28: 1981-1991, 2010), and passed the standard tests for pluripotency; they formed teratomas and expressed pluripotent stem cell markers. After removal of basic FGF from the growth media, some of the retinal spPSC lines spontaneously re-differentiated back towards a retinal epithelial cell lineage. Approximately 60% of the cells that spontaneously differentiate from human fetal retinal epithelial spPSCs cells are retinal epithelial cells, compared to between 5 and 16% retinal epithelial cells from spPSCs from human fetal lung fibroblasts, from human foreskin fibroblasts, or human ESC cells. However, one of the 3 spPSCs cells from human fetal retinal epithelial cells failed to differentiate into retinal epithelial cells at all. Kim et. al. (*Nature*, 467(7313):285-90, 2010), reprogrammed bone marrow progenitor cells and dermal fibroblasts from aged mice using retroviral introduction of Oct4, Sox2, Klf4 and Myc. All of their resulting stem cells lines demonstrated pluripotency using the criteria typically applied to human samples. Subsequent differentiation of their reprogrammed pluripotent stem cells demonstrated that hematopoietic sources re-differentiated towards hematopoietic lineages more readily than fibroblast sources, and similarly, fibroblast sources re-differentiated towards mesenchymal lineages more readily than hematopoietic sources. The authors also showed that this propensity to re-differentiate preferably towards their somatic lineage of origin could be overcome partially by differentiation towards the hematopoietic lineage followed by another round of pluripotent reprogramming and then additional differentiation. For instance, reprogrammed cells derived from neural progenitor cells were differentiated towards hematopoietic lineages then reprogrammed to pluripotency and showed higher hematopoietic colony formation than neural progenitors that were differentiated towards neural cells, reprogrammed and then differentiated towards hematopoietic cells.

Similar observations of a preference for reprogrammed cells to re-differentiate towards their cell type of origin have been made using non-viral reprogramming of human fetal neural progenitor cells (*PLoS One.*, 4: e7076-e7088, 2009). The resulting reprogrammed cells expressed several markers of pluripotency, markers for all three germ layers, and were able to form embryoid bodies in culture and teratomas, however, using GeneChip analysis, the authors demonstrated that the reprogrammed neural progenitor cells retained some expression of neural stem cell genes. Polo et. al. (*Nat Biotechnol*, 28: 848-855, 2010), derived pluripotent reprogrammed cells from mouse tail tip derived fibroblasts, splenic B cells, bone marrow granulocytes and skeletal muscle precursors. Autonomous differentiation studies indicated that splenic B cell and bone marrow granulocyte reprogrammed spPSCs cells gave rise to hematopoietic progenitors more efficiently than fibroblast or skeletal muscle derived spPSCs cells. Interestingly, serial passage of these various spPSCs cell lines led to the abrogation of genetic and methylation differences by passage 16, and the cells also then demonstrated equivalent differentiation efficiencies, in contrast to the earlier results at passage 4. Interestingly, this phenomenon of differential differentiation potential is not restricted to reprogrammed somatic cells, but has also been observed for embryonic stem cells lines, which have been found to have differing genetic signatures and spontaneous preference for differentiation towards certain cell lineages (*Nat Biotechnol.*, 26: 313-315, 2008) (*Hum Reprod Update.*, 13: 103-120, 2007) (*Dev Biol.*, 307:446-459, 2007) (*BMC Cell Biol*, 10:44, 2009).

Stem cells can be characterized and isolated by specific antigens expressed on their surface. Pluripotent stem cells can be characterized by the expression of stage-specific embryonic antigen (SSEA), the transcription factors Oct4 and Nanog and other markers, among other methods. Embryonic stem cell derived fibroblasts and adult fibroblasts and other cells have been reprogrammed to a pluripotent state by fusion with embryonic stem cells (Cell 126: 652-655, 2006 and Stem Cell Rev, 2: 331-340, 2006), by the addition of 4 genes using retroviral transfection techniques (Cell 126: 663-676, 2006), by a single cassette or bicistronic lentiviral transfection methods (Stem Cells 27: 543-549, 2009 and Stem Cells 27: 1042-1049, 2009), and by endogenous stimulation of pluripotency required transcription factors (Stem Cells 27: 3053-3062, 2009). Induction or maintenance of pluripotency could also be achieved by modifying methylation or polyadenylation status of the genome (PLoS One 4: e8419, 2009), by microRNAs (Dev Biol. 344: 16-25, 2010), small molecule activators of required transcription factors, epigenetic reprogramming (Regen Med. 2: 795-816, 2007), by protein-based reprogramming (Blood 116: 386-395, 2010), by addition of culture supernatant or cell extracts from pluripotent cells in culture, chemical or radiation or other means of genetic mutation to reactivate pluripotency genes, or addition of growth factors or cytokines or cellular signaling moieties that induce or maintain endogenous pluripotent states. The use of retroviruses to reprogram cells to pluripotent states presents dangers that recall the gene therapy trials for immune deficiency. Excision techniques such as Cre-lox or the piggyBac transposon methods have been used to eliminate the retrovirus after successful reprogramming (Curr Opin Biotechnol. 20: 516-521, 2009). Cloning techniques such as SCNT and parthenogenesis (PGA) (Cell Reprogram. 12: 105-113, 2010) have also been used to generate reprogrammed pluripotent stem cells (Nature 450:497-502, 2007).

Significant amounts of resources—economic, intellectual and labor—have been invested in discovering various sources of pluripotent stem cells, primarily in the hopes that these stem cells would be appropriate for human regenerative medicine therapy. Unfortunately, except for the adult VSELs (*Stem Cell Rev* 4:89-99, 2008), all of the pluripotent stem cells isolated to date are thwarted because of problems with teratoma formation, tumor formation, and even neoplastic properties. Therefore, some utility for these pluripotent stem cells is needed in order to take advantage of the economic, intellectual and labor investment that has been made over the past 15 years or so.

Stem cells can be induced to differentiate towards somatic cell types in culture by the addition of various growth factors to the culture (*Blood* 85:2414-2421, 1995), by altering nutrients in the culture media, by manipulating culture conditions such as oxygen tension (*BMC Cell Biol.* 11:94, 2010) or temperature, or by culturing the stem cells on various extracellular matrices, among other methods as are known to those in the field of cellular biology and cell differentiation. For instance, retinoic acid, TGF-β, bone morphogenic proteins (BMP), ascorbic acid, and beta-glycerophosphate lead to production of osteoblasts; indomethacin, IBMX (3-isobutyl-1-methylxanthine), insulin, and triiodothyronine (T3) lead to production of adipocytes; aFGF, bFGF, vitamin D3, TNF-β and retinoic acid lead to production of myocytes (WO/1999/049015) March 1998). Differentiation strategies to obtain various somatic cell lines from stem cells at various stages are well known to those in the field of stem cell biology.

Stem cell therapy is being investigated and perfected for the treatment of many human diseases. Clinical trial information contained in the NIH website lists over 3000 stem cell investigations. Diseases under evaluation include: hematological malignancies, leukemias, lymphomas, cancers, osteopetrosis, aplastic anemia and cytopenias, sickle cell disease and thalassemia, limbal stem cell deficiency, breast cancer, acute myocardial infarction, coronary artery disease, peripheral vascular disease, heart failure, type I diabetes mellitus, type 2 diabetes mellitus, stroke, spinal cord injury, neuroblastoma, multiple sclerosis, systemic sclerosis, lupus erythematosus, chronic wound healing, burns, fracture healing, cartilage repair, CNS tumors, osteoarthritis, renal failure, Parkinson's Disease, myelomas, diabetic foot, liver and biliary cirrhosis, dilated cardiomyopathy, anemia, retinitis pigmentosa, Crohn's Disease, diabetic neuropathy, mastocytosis, ovarian cancer, epilepsy, myasthenia gravis, autoimmune diseases, granulomatous disease, osteonecrosis, liver failure, PMD disease, lypodystrophy, demyelinating diseases, cartilage defects, retinal disease, lupus nephritis, Alzheimer's Disease, traumatic brain injury, sarcoma, myositis, hyperglycemia, macular degeneration, ulcerative colitis, muscle degeneration, and others.

Stem cells can be isolated using various markers known to those practicing in the field. For instance, a list of common stem cell markers can be found at http://stemcells.nih.gov/info/scireport/appendixe.asp#eii. Neural stem cells can be isolated by the use of CD133; mesenchymal stem and progenitor cells by the use of Bone Morphogenic Protein Receptor (BMPR); hematopoietic stem cells by CD34; mesenchymal stem cells by the combination of CD34+Sca1+Lin− markers; hematopoietic and mesenchymal stem cells by ckit, Stro1, or Thy1; neural and pancreatic progenitors by nestin; ectoderm, neural and pancreatic progenitors by vimentin; and other markers.

The present invention further provides methods to safely reprogram and re-differentiate somatic cells for regenerative medicine. Useful somatic cells can include fully differentiated somatic cells, progenitor cells, or more primitive stem cells. Depending on the organ that requires regenerative therapy, more primitive stem cells may be more or less accessible by organ puncture, biopsy, scrapings or surgical access. Use of more primitive stem cells is preferable when access to these stem cells is possible. Less preferable, but more preferable than fully differentiated somatic cells, is the use of progenitor cells.

Isolation of somatic cells from the specific organ targeted for treatment, reprogramming of those somatic cells, short term expansion in culture assuring that the intrinsic 'memory' of the spPSCs is maintained, followed by re-differentiation in culture to the cell type of origin followed by therapeutic application allows for pluripotent stem cell methods to be used to treat patients with reduced dangers of tumor or teratoma formation.

Reprogrammed somatic cells could be used between passages 1 and 12, most preferably at passage 4. The reprogrammed somatic cells could be differentiated towards the cell type for desired regeneration according to standard cell biology and differentiation techniques. The resulting therapeutic cell could be administered by intravenous, intraarterial, intramuscular or other injection methods using standard injection techniques that may include catheters such as the NOGAStar or MyoStar injection catheters or other approved catheter injection device. Alternatively, the therapeutic cells may be administered to the target tissue by minimally invasive or more invasive surgical methods. The therapeutic cells may be administered in a buffer composition containing autologous human serum albumin between 0 and 15%, most preferably 5%. For treating disease of the central nervous system, the therapeutic cells would preferably be buffered using autologous cerebrospinal fluid. The therapeutic cells may also be administered through the use of a scaffold such as collagen, fibrinogen or other extracellular matrix or combination of extracellular matrices, or by the use of a thread such as created using alginate or other standard methods, to hold the cells in place and maintain contact with the organ that requires regenerative repair.

Preferably A minimum of 500 therapeutic cells will be administered, and commonly cell therapy will utilize 15 million to 500 million cells. More preferably, between 15 million and 100 million cells will be administered for optimal benefit.

As an example, for cell therapy for neural diseases such as Alzheimer's, Parkinson's, stroke, Huntington's Disease, multiple sclerosis, paralysis and other diseases of the central nervous system (CNS), would preferably isolate olfactory mucosa using rigid endoscopes as published (*J Spinal Cord Med.* 29:191-203, 2006). Neural stem and progenitor cells or olfactory ensheathing cells are isolated from the olfactory mucosa according to methods well known to those practicing in the field of regenerative medicine. Alternatively, neural crest stem cells can be isolated from human hair follicles (*Folia Biol.* 56:149-157, 2010). Most preferably, neural stem cells are reprogrammed by the addition of defined factors, expanded and passaged for 4 passages, re-differentiated towards specific central nervous system cell types by the addition of defined factors, and then administered to the patient for regenerative therapy.

The invention provides methods to safely reprogram and re-differentiate somatic cells for regenerative medicine. Useful somatic cells can include fully differentiated somatic cells, progenitor cells, or more primitive stem cells. Depending on the organ that requires regenerative therapy, more primitive stem cells may be more or less accessible by organ puncture, biopsy, scrapings or surgical access. Use of more primitive stem cells is preferable when access to these stem cells is possible. Less preferable, but more preferable than fully differentiated somatic cells, is the use of progenitor cells.

For spinal injury repair, olfactory mucosa is removed by rigid endoscope, neural stem cells are isolated using the neurosphere assay first described in 1992 by Reynolds and Weiss (*Science,* 255:1707-1710, 1992), epidermal growth factor (EGF) and basic fibroblast growth factor (bFGF) are added to the cells that survive several days of culture of the olfactory mucosa to stimulate neurosphere growth, and neural stem cells are recoverable within 7 to 10 days of culture. The resulting neural stem cells are reprogrammed by the addition of episomal vectors for the delivery of OCT4 and NANOG with hygromycin selection for 5-7 days. The cells are passaged and expanded until passage 4 to obtain integration-free colonies, and then differentiated towards olfactory ensheathing and stem-like neural progenitor cells using autologous cerebrospinal fluid or defined factors. The damaged spinal cord is exposed during surgery using a standard midline incision and a posterior midline myelotomy, scar tissue is removed as permissible, the therapeutic cells are buffered in autologous cerebrospinal fluid, seeded onto a bioactive scaffold and applied directly to the injured spinal cord.

EXAMPLES

Example 1

Genetic Modification of Patient Specific Synthetically Produced Pluripotent Stem Cells for Recombinant Protein Production Synthetically produced pluripotent stem cells (spPSCs) such as SCNT or PGA or ANT-OAR or iPSCs are used from patients for genetic modification to induce biologic production. SCNT derived stem cells are prepared by transferring the nucleus of a patient's cell into an enucleated oocyte that has been prepared. ANT-OAR derived stem cells are prepared by genetically modifying a patients nuclear DNA prior to transferring the modified nucleus into an enucleated, prepared oocyte. iPSCs derived stem cells are prepared by reprogramming the patient's cells using genetic modification, activators of pluripotent transcription factors, epigenetic modification or other methods known in the art as described above. The resulting patient specific synthetically produced stem cell line is 'banked' as a master cell bank and a working bank for subsequent genetic modification for biologic production.

Germ cells are generated from pluripotent stem cells using monolayer culture, the formation of embryoid bodies (EBs), co-aggregation with BMP4-producing cells, the use of testicular or ovarian cell-conditioned medium, or EB formation with recombinant human bone morphogenetic proteins (BMPs). Germ cells are identified by the expression of marker genes that can include PR domain containing 1, with ZNF domain (PRDM1, also known as BLIMP1), PR domain containing 14 (PRDM14), protein arginine methyltransferase 5 (PRMT5), DPPA3, IFITM3, GDF3, c-KIT, chemokine (C—X—C motif) receptor 4 (CXCR4), NANOS1-3, DAZL, VASA, PIWI family genes (PIWIL1 and PIWIL2, known as HIWI and HILI in humans, respectively), Mut-L Homologue-1 (MLH1), synaptonemal complex protein 1 (SCP1), and SCP3. The resulting germ cells are transfected with a gene of interest, such as Factor VIII, according to methods generally used for the manufacture of recombinant Factor VIII.

Example 2

Genetic Modification of Patient Specific Synthetically Produced Pluripotent Stem Cells for Recombinant Insulin Production Synthetically produced pluripotent stem cells (spPSCs) such as SCNT or PGA or ANT-OAR or iPSCs derived stem cells are used from patients for genetic modification to induce biologic production. SCNT derived stem cells are prepared by transferring the nucleus of a patient's cell into an enucleated oocyte that has been prepared. ANT-OAR derived stem cells are prepared by genetically modifying a patients nuclear DNA prior to transferring the modified nucleus into an enucleated, prepared oocyte. iPSCs derived stem cells are prepared by reprogramming the patient's cells using genetic modification, activators of pluripotent transcription factors, epigenetic modification or other methods known in the art as described above. The resulting patient specific synthetically produced stem cell line is 'banked' as a master cell bank and a working bank for subsequent genetic modification for biologic production.

Expression of insulin precursors in patient specific stem cells is performed according to methods generally used for the manufacture of insulin in *S. cerevisiae*: [Kjeldsen T., et al., "Engineering-enhanced protein secretory expression in yeast with application to insulin". 21, May 2002, *J Biol Chem.*, 277:18245-18248 (May 2002); Zhang B., et al., "Intracellular retention of newly synthesized insulin in yeast is caused by endoproteolytic processing in the Golgi complex", *J Cell Biol.*, 153:1187-1198 (June 2001); and Kristensen C. et al., "Alanine scanning mutagenesis of insulin"., *J Biol Chem.*, 272:12978-12983 (May 1997)], or *E. Coli* [Son Y J., et al. "Effects of beta-mercaptoethanol and hydrogen peroxide on enzymatic conversion of human proinsulin to insulin"., *J. Microbiol Biotechnol.*, 18:983-989 (May 2008)], then processed and purified according to standard methods. The insulin precursor expressing patient specific cell line is 'banked' as a master cell bank and a working cell bank for subsequent insulin production.

Example 3

Generation of Beta-Cells for Insulin Production Using Genetic Modification of Patient Specific Synthetically Produced Pluripotent Stem Cells To produce insulin, somatic cells are used from patients for genetic modification to produce spPSCs and these are used to induce biologic production. The spPSCs derived stem cells are prepared by reprogramming the patient's cells using genetic modification, activators of pluripotent transcription factors, epigenetic modification or other methods known in the art. The resulting patient specific stem cell line is 'banked' as a master cell bank and a working bank for subsequent genetic modification for biologic production. Or endogenous pluripotent stem cells (ePSCs) can be isolated according to techniques described above and banked.

Expression of insulin precursors in patient specific stem cells is performed according to methods generally used for the manufacture of insulin in *S. cerevisiae* or *E. coli* as described above. Following gene transfection with the appropriate insulin gene constructs, the cells are differentiated towards the beta-cell lineage following standard protocols found in [Shi, Y., et. Al. "Inducing embryonic stem cells to differentiate into pancreatic beta cells by a novel three-step approach with activin A and all-trans retinoic acid". Stem Cells., 23:656-662 (2005); or Tateishi, K., et. Al. "Generation of insulin-secreting islet-like clusters from human skin fibroblasts"., J Biol Chem., 283:31601-31607 (2008)]

The resulting expressed biologic product is then processed and purified according to standard methods. The resulting patient specific insulin precursor expressing stem cell line is 'banked' as a master cell bank and a working bank for subsequent genetic modification for biologic production.

Alternatively, the resulting patient specific stem cells are differentiated towards the beta-cell lineage following standard protocols found in Shi et. Al. id. Or Tateishi et. Al. id of the Beta Cell Biology Consortium id. Once differentiated, expression of insulin precursors in patient specific stem cells is performed according to methods generally used for the manufacture of insulin in *S. cerevisiae*: or *E. Coli* as discussed above. The resulting expressed biologic product is then processed and purified according to standard methods.

Example 4

Isolation of Adult (Somatic) Antibody Producing Cells for Reprogramming and Transfection to Produce Biologic Antibody Therapeutics Antibody producing B cells are isolated from peripheral blood, bone marrow and other readily accessible hematopoietic cell sources for the purpose of generating patient specific manufacturing cell. lines to produce therapeutic antibody biologics. B cells are isolated using available kits based on CD19 expression (StemCell Technologies). Limiting dilution or cell sorting methods may be employed to select cells producing the highest levels of immunoglobulin (Ig). After brief expansion, the clonal high Ig producing cell is reprogrammed to a pluripotent or progenitor state using standard reprogramming techniques. The resulting patient specific stem cells are transduced with the desired antibody gene constructs using standard molecular biology techniques and methods. The resulting expressed antibody therapeutic is processed and purified according to state of the art biotechnology methods, whether publicly available or confidentially maintained by the owners of the composition of matter for the antibody therapeutic. Methods to obtain the desired purified antibody product include ion exchange chromatography.

Example 5

Isolation of Adult (Somatic) Antibody Producing Cells for Reprogramming, and Transfection to Produce Biologic Antibody Therapeutics with Redifferentiation to Somatic Antibody Producing Cells Antibody producing B cells are isolated from peripheral blood, bone marrow and other readily accessible hematopoietic cell sources for the purpose of generating patient specific manufacturing cell lines to produce therapeutic antibody biologics. Limiting dilution or cell sorting methods may be employed to select cells producing the highest levels of immunoglobulin (Ig). After brief expansion, the clonal high Ig producing cell is reprogrammed to a pluripotent or progenitor state using standard reprogramming techniques. The resulting patient specific stem cells are transduced with the desired antibody gene constructs using standard techniques and methods. Following gene modification, the pluripotent patient specific cell line is differentiated to a mature antibody producing B cell by culture in the presence of CD40L, BAFF, toll-like receptor activation (TLR) [Hayashi E. A., et al. "TLR4 promotes B cell maturation: independence and cooperation with B lymphocyte-activating factor"., *J Immunol.*, 184:4662-4672 (2010), or other B cell maturation factor as is known in the art such as B-cell receptor (BCR) activation and Notch-receptor ligand family activation [Palanichamy A. et al. "Novel human transitional B cell populations revealed by B cell depletion therapy". 10, May 2009, J Immunol., Vol. 182, pp. 5982-5993 (2009); Thomas M. D. et al., "Regulation of peripheral B cell maturation"., *Cell Immunol.*, 239:92-102 (2006).

Titers and affinity of the therapeutic antibody can be improved by the use of methods such as morphogenic techniques as described Li J., et al., "Human antibodies for immunotherapy development generated via a human B cell hybridoma technology"., *Proc Natl Acad Sci*, 103:3557-3562 (2006). The resulting expressed antibody therapeutic is processed and purified according to state of the art biotechnology methods, whether publicly available or confidentially maintained by the owners of the composition of matter for the antibody therapeutic.

Alternatively, the pluripotent patient specific cell line is differentiated to a mature antibody producing B cell by culture in the presence of CD40L, BAFF, toll-like receptor activation (TLR) (See Hayashi, et al. id)., or other B cell maturation factor as is known in the art such as B-cell receptor (BCR) activation and Notch-receptor ligand family activation. (See Palanichamy A. et al. id., and Thomas, M. D. et al. id.) Titers and affinity of the therapeutic antibody can be improved by the use of methods such as morphogenic techniques as described (See Li, et al. id.).

The resulting patient specific antibody producing cells are transduced with the desired antibody gene constructs using standard techniques and methods. The resulting expressed antibody therapeutic is processed and purified according to state of the art biotechnology methods, whether publicly available or confidentially maintained by the owners of the composition of matter for the antibody therapeutic.

Example 6

Generation of Patient Specific Cell Lines for Production of High Activity ADCC Antibodies N-acetylglucosamine (GlcNac) post-translational modification of immunoglobulins is important for antibody-dependent cell-mediated toxicity (ADCC), and non-fucosylated GlcNac residues have the highest affinity for Fc gamma receptors Mori K., et al., "Non-fucosylated therapeutic antibodies: the next generation of therapeutic antibodies"., *Cytotechnology.*, 55:109-114 (2007).

Therefore, when an antibody therapeutic with high levels of ADCC is desired, a patient specific cell line capable of transferring GlcNac at the appropriate levels and leaving the GlcNac non-fucosylated is desirable. Carcinoma cells are known to express higher levels of GMD and therefore, since cancer stem cells and pluripotent cells have similar genetic signatures, pluripotent cells may also be suspected to express high levels of GMD, the enzyme responsible for post-translational GlcNac attachment. Among normal tissues, colon and pancreas express the highest levels of GMD. Lack of FUT8, which is responsible for the enzyme that fucosylates antibodies would be desirable in a patient specific stem cell line for therapeutic antibody production dependent on ADCC activity for efficacy, such as Rituximab or Herceptin. For instance, monoclonal antibodies produced in rat hybridoma YB2/0 cells have 50 fold higher ADCC activity than the same monoclonal antibodies produced using CHO cells. Adipose-derived stem cells and germ cell lines, as well as B cell lymphomas, express higher than average levels of FUT8, while hematopoietic stem cells (HSC), immature B cells, normal skeletal muscle express lower than average FUT8.

Hematopoietic stem cells are isolated according to standard methods from bone marrow aspirates, or whole blood apheresis with or without prior treatment with stem cell mobilizing agents. The isolated HSC are subsequently reprogrammed to pluripotency as previously described. The resulting patient specific stem cells are transduced with the desired antibody gene constructs using standard techniques and methods. Following gene transfection, the pluripotent patient specific cell line is differentiated to a mature antibody producing B cell by culture in the presence of CD40L, BAFF, toll-like receptor activation (TLR) (See Hayashi E. A., et al., id.), or other B cell maturation factor as is known in the art such as B-cell receptor (BCR) activation and Notch-receptor ligand family activation (See Palanichamy A. et al. id., and Thomas, M.D. et al. id.). Titers and affinity of the therapeutic antibody can be improved by the use of methods such as morphogenic techniques as described (See Li, et al. id.). The resulting expressed antibody therapeutic is processed and purified according to state of the art biotechnology methods, whether publicly available or confidentially maintained by the owners of the composition of matter for the antibody therapeutic.

Alternatively, antibody producing B cells are isolated from peripheral blood, bone marrow and other readily accessible hematopoietic cell sources for the purpose of generating patient specific manufacturing cell lines to produce therapeutic antibody biologics. Limiting dilution or cell sorting methods may be employed to select cells producing the highest levels of immunoglobulin (Ig). After brief expansion, the clonal high Ig producing cell is reprogrammed to a pluripotent or progenitor state using standard reprogramming techniques. The resulting patient specific stem cells are transduced with the desired antibody gene constructs using standard techniques and methods. Following gene modification, the pluripotent patient specific cell line is differentiated towards an HSC, immature B cell or skeletal muscle cell for production of therapeutic antibodies that are low or lacking fucose.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

BRIEF DESCRIPTION OF THE DRAWINGS

Preferred and alternative examples of the present invention are described in detail below with reference to the following drawings:

FIGURE one depicts the layers resulting from gradient centrifugation of whole blood.

What is claimed is:

1. A method for producing an isolated therapeutic recombinant biologic polypeptide or protein for treating a disease comprising transfecting a synthetically-produced Pluripotent Stem Cell (spPSC) with a nucleic acid that encodes for said therapeutic recombinant biologic polypeptide or protein, under conditions wherein the polypeptide or protein is expressed by said spPSC, and the polypeptide or protein is then isolated from the spPSC, and the spPSC is produced from a cell of an animal.

2. The method of claim 1, wherein the therapeutic recombinant biologic polypeptide or protein is selected from the group consisting of: growth hormones, cytotoxic biologics, and monoclonal antibodies.

3. The method of claim 1 wherein the therapeutic biologic polypeptide or protein is selected from the group consisting of erythropoietin, factor VIII, factor IX, thrombin, an antibody or antibody fragment, alpha interferon, interferon alpha 2A and 2B, beta interferon, growth hormone, antihemophilic factor, G-CSF, GM-CSF, a soluble receptor, TGF-β, bone morphogenic proteins (BMP), TGFα, interleukin 2, β-glucocerebrosidase or an analogue thereof, alpha1-proteinase inhibitor, fibrin, fibrinogen, von Willebrand factor, imiglucerase, agalsidase beta, laronidase, glucosidase alpha, thyrotropin alpha, and thymosin alpha.

4. The method of claim 2 wherein the antibody or antibody fragment binds to a target, wherein said target is selected from the group consisting of a tumor necrosis factor (TNF) molecule, a tumor necrosis factor receptor (TNFR), a growth factor receptor, a vascular endothelial growth factor (VEGF) molecule, interleukin 1, interleukin 4, interleukin 6, interleukin 11, interleukin 12, gamma interferon, receptor activator of nuclear factor kappa-B ligand (RANKL) and Blys.

5. The method of claim 2 wherein said soluble receptor binds to a target selected from the group consisting of TNFα, TNFβ and Blys.

6. The method of claim 1 further comprising immortalizing the transfected spPSC.

7. The method of claim 6 further comprising inducing differentiation of the transfected, immortalized spPSCs.

8. The method of claim 1 further comprising inducing differentiation of the transfected spPSCs.

9. The method of claim 8 further comprising immortalizing the transfected, differentiated cells.

10. The method of claim 1 wherein the spPSC is selected from the group consisting of transfected non-pluripotent cells, pluripotent stem cells produced by Somatic cell nuclear transfer (SCNT pluripotent stem cells), pluripotent stem cells produced by Altered nuclear transfer, oocyte assisted reprogramming (ANT-OAR pluripotent stem cells) and pluripotent stem cells produced by parthenogenesis (PGA pluripotent).

* * * * *